United States Patent [19]

Walsh et al.

[11] Patent Number: 4,612,664
[45] Date of Patent: Sep. 16, 1986

[54] ARTIFICIAL SPEECH AID TONE GENERATING DEVICE

[75] Inventors: John J. Walsh, La Crescent; Michael W. Walsh, Shoreview, both of Minn.

[73] Assignee: Dacomed Corporation, Minneapolis, Minn.

[21] Appl. No.: 725,946

[22] Filed: Apr. 22, 1985

[51] Int. Cl.$^4$ ................................................ A61F 1/20
[52] U.S. Cl. ............................................ 381/70; 623/9
[58] Field of Search ......... 381/70; 129/114 A, 115 A; 3/1.3

[56] References Cited

U.S. PATENT DOCUMENTS

| | | | |
|---|---|---|---|
| 1,836,816 | 12/1931 | Riesz | 3/1.3 |
| 2,041,487 | 5/1936 | Riesz | 381/70 |
| 3,066,186 | 11/1962 | Trammell | 381/70 |
| 3,084,221 | 4/1963 | Cooper | 381/70 |
| 3,508,000 | 4/1970 | Snyder | 381/70 |
| 3,766,318 | 10/1973 | Webb | 381/70 |
| 4,109,103 | 8/1978 | Zagoruiko et al. | 381/70 |
| 4,223,411 | 9/1980 | Schoendorfer et al. | 3/1.3 |
| 4,292,472 | 9/1981 | Lennox | 3/1.3 |
| 4,338,488 | 7/1982 | Lennox | 381/70 |
| 4,489,440 | 12/1984 | Chaoui | 381/70 |

Primary Examiner—Gene Z. Rubinson
Assistant Examiner—L. C. Schroeder
Attorney, Agent, or Firm—Merchant, Gould, Smith, Edell, Welter & Schmidt

[57] ABSTRACT

The present invention consists of a novel device for the production of a tone suitable for use in artificial speech aids. Artificial speech aids provide for a method of speech, for individuals who have either temporarily or permanently lost the use of their vocal cords, through the production and delivery of a substitute vocal tone to the user's oral cavity, thereby allowing such individuals to speak through articulation of the tone into words. The present invention concerns a novel device for the production of the substitute vocal tone. In the present device, the tone is produced by actuating a solenoid reed valve to a sufficient frequency that sound is produced, which sound is then amplified by the passage of pressurized air through the valve as it is actuated. The invention herein includes an electrical pulse generator for producing the pulsed electrical signal needed to operate the solenoid reed valve.

5 Claims, 3 Drawing Figures

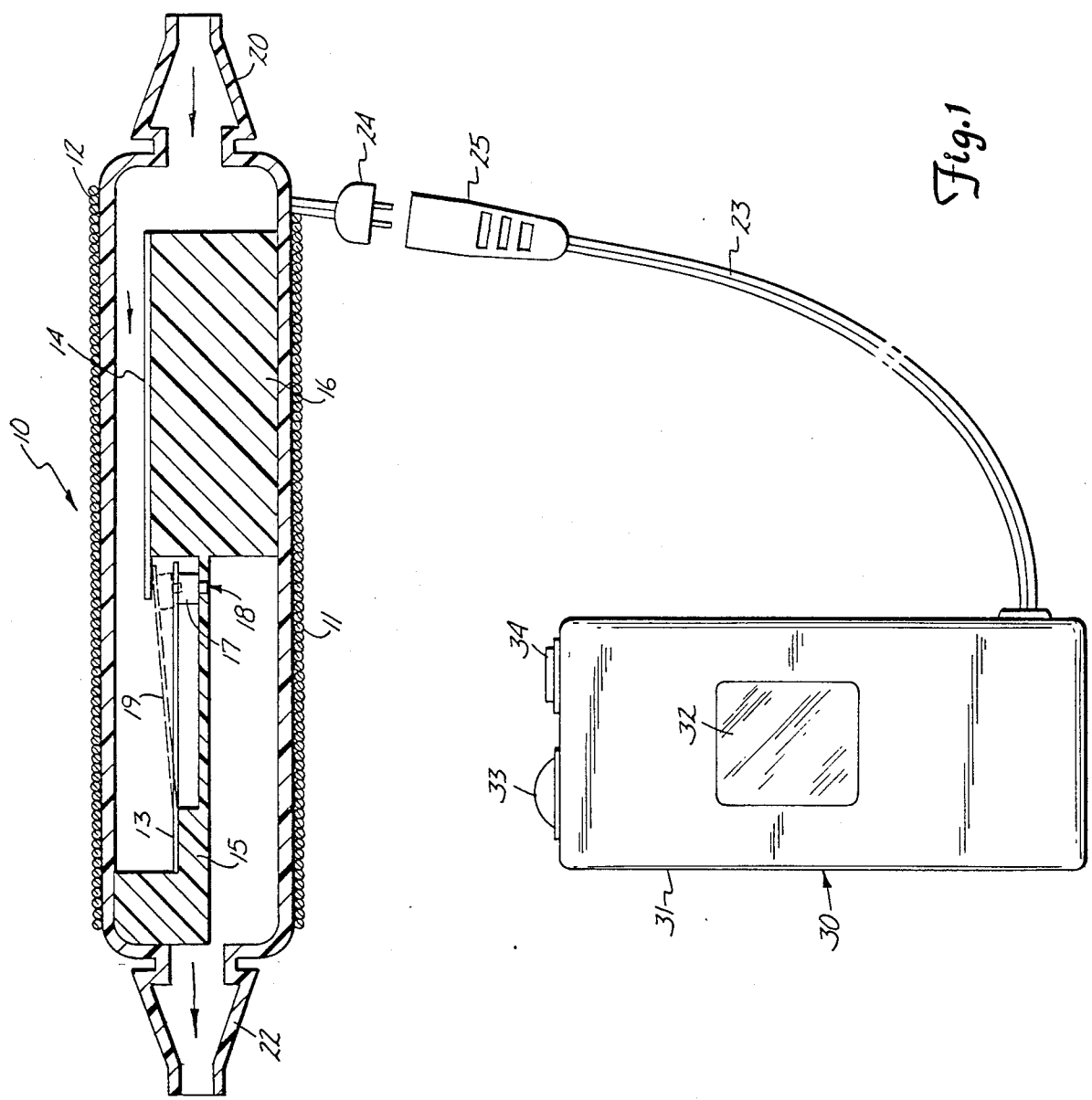

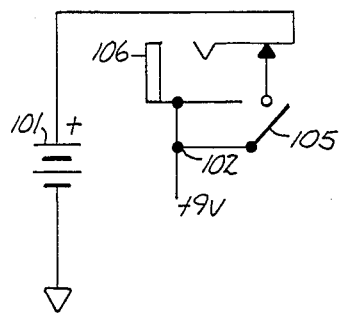
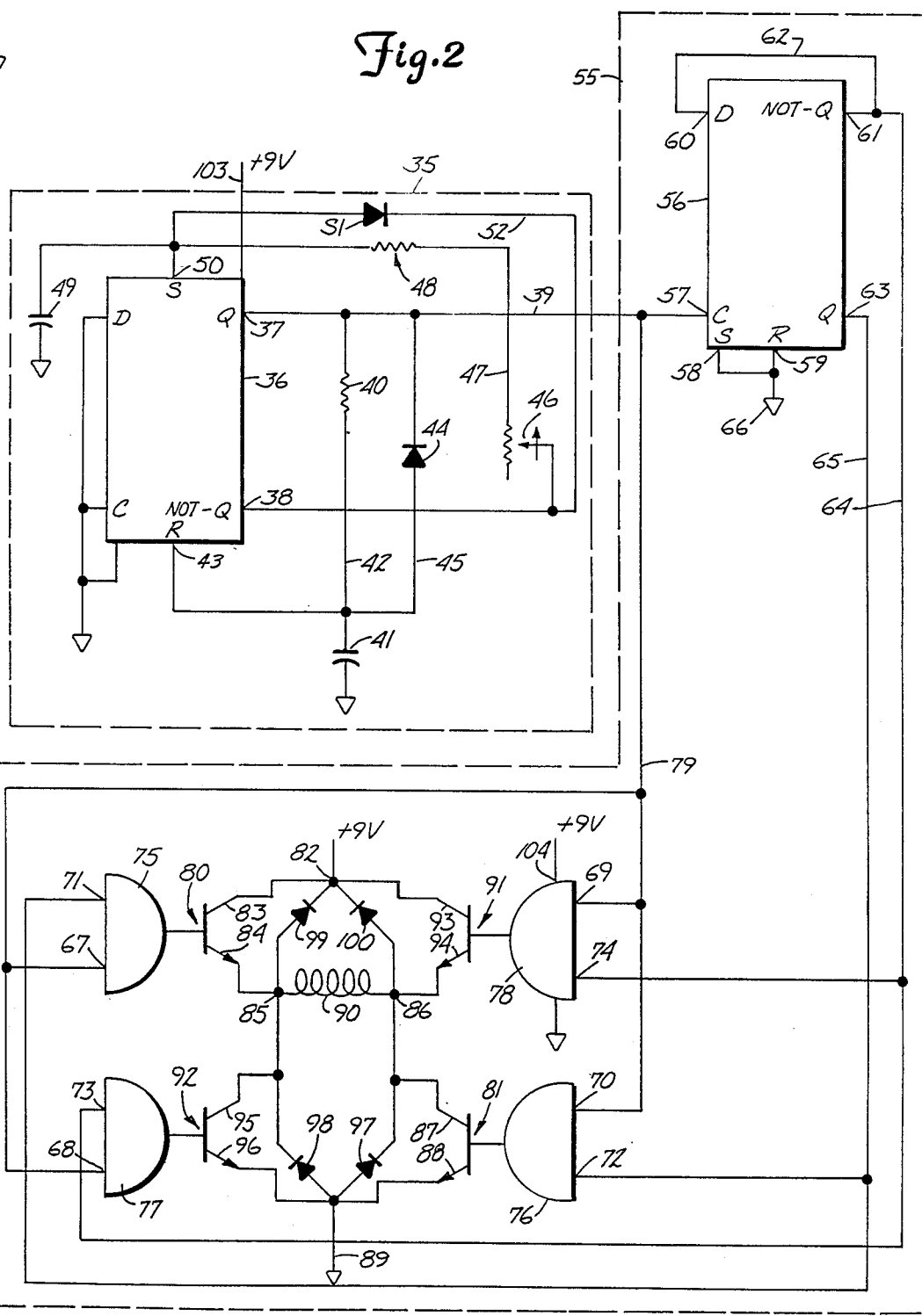

ARTIFICIAL SPEECH AID TONE GENERATING DEVICE

BACKGROUND OF THE INVENTION

1. Field of the Invention

The present invention relates generally to artificial speech aids, and in particular to the means for tone generation used therein.

2. Description of the Prior Art

Artificial speech aids enable individuals that have lost the use of their vocal cords to speak. These devices function to produce a substitute vocal sound that, when delivered to the user's oral cavity, can be articulated into words in the normal manner. Artificial speech devices essentially consist of a means for generating a tone, and a means for delivering that tone to the user's oral cavity.

Present art speech devices generate the substitute vocal sound either electrically or pneumatically. An electrically operated tone generating means typically produces sound by vibrating a diaphragm electromagnetically to a suitable frequency. For an example of an electrically operated tone generator, see U.S. Pat. No. 3,066,186 to Trammel. In a pneumatic device, pressurized air flows through the tone generating means, vibrating a reed or diaphragm contained therein, thereby producing the artificial speech sound. For an example of a pneumatically operated tone generating means, see U.S. Pat. No. 4,223,411 to Schoendorfer et al.

The tone delivery means, in general terms, is a conduit, connected to the tone generating means, through which the tone is propagated and thereby delivered to the user's oral cavity. A common tone delivery means is the intra-oral tube, which is simply a hollow, flexible, plastic tube which delivers the tone through insertion directly into the user's mouth. Another delivery means consists of a small diameter plastic tube that is nasally inserted, and through which the 5 tone is delivered to the user's oral cavity. For individuals that have a stoma or opening in their throat, as results from a tracheostomy, suitable conduit means exist for delivery of the tone through the stoma, and into, and up the trachea, to the oral cavity.

Electrically operated artificial speech aids have the advantage of being small in size, and are generally battery operated and thus portable. However, the sound energy produced by current art electrically operated tone generators dissipates quickly. Therefore, to insure the delivery of a tone of sufficient volume to produce audible speech, the tone must be delivered directly into the user's oral cavity. This restriction generally requires the use of an intra-oral tube, as described previously. Use of an intra-oral tube, however, requires the presence of the tube in the user's mouth during speech, which presents articulation problems for certain word sounds and can become a nuisance to the user when held in the mouth overprolonged periods of time. Furthermore, an intra-oral tube requires a free hand or support means to position it properly in the user's mouth. Many individuals that can benefit from the use of an artificial speech aid are not physically capable of holding a tone delivery means, and use of a support device can burden the user with additional unnatural apparatus.

Pneumatic tone generators have the advantage of being compatible with a wider range of tone delivery means than electronic tone generators. The pressurized air which vibrates the sound producing mechanisms also acts to amplify and "carry" the tone, thereby enhancing the tone delivery capacity of the particular delivery means. For example, a pnuematic tone generator can be used with a nasally inserted delivery means, which delivery means is longer than an intra-oral tube, as a nasally inserted delivery means must be able to reach from the exterior of the user's nasal pharynx to the posterior oral pharynx, to provide for tone delivery. Thus, due to its length, a nasal tube delivery means does not provide an adequate acoustic conduit for the propagation of the lower volume sound associated with an electronically produced tone, as such tone would quickly dissipate and would not provide for audible speech without the sound enhancement provided by a pressurized air flow. In addition, a pneumatic speech system that includes a nasal delivery means eliminates the articulation and nuisance problems associated with intra-oral tube systems, and eliminates the necessity for a free hand or support device to hold the delivery means.

Another advantage of a pressurized air flow concerns the fact that various tone delivery means can become blocked with mucous or saliva and rendered ineffective, whereas an air flow passing through the particular delivery means can prevent this clogging. However, a disadvantage of pneumatic tone generators lies in the fact that the air flow needed to vibrate the sound producing mechanism can be of such a volume so as to cause excessive drying of the moist tissue of the oral cavity surrounding the point of exit of the air from the tone delivery means, and also may result in air swallowing and stomach distention. This drying can necessitate periodic removal or disuse of the tone delivery means.

SUMMARY OF THE INVENTION

The present invention resides in a novel apparatus for tone generation. The present invention combines both pneumatic and electronic means for tone generation, thereby improving the state of the art of tone generators used in artificial speech systems. Basically, and in general terms, the present invention includes a solenoid reed valve means and an electronic pulse generating means, which generating means produces the electrical signal used to actuate the valve means.

Essentially, operation of the present tone generator involves actuating the reed of the valve means to a sufficient frequency so that the rapid flexing of the reed produces a tone. A pressurized air source connected to one end of the valve provides an air flow that passes through the valve means amplifying the tone produced therein. The tone and pressurized air then enter a tone delivery means, connected to the end of the valve opposite that of the pressurized air source, for delivery to the user's oral cavity, wherein the tone is articulated into speech.

It was surprisingly discovered that, when actuated to a sufficient frequency, a solenoid reed valve would produce a tone suitable for use in an artificial speech system. Normally, a solenoid reed valve is used for low frequency on/off regulation of a liquid or gas flow, but is not for any purpose operated to produce a sound. This discovery then led to the further innovation of passing pressurized air through the valve to amplify the sound, and thus of combining both the electrical and pneumatic tone producing principles used in artificial speech aids.

A major advantage of the tone generator of the present invention is its compatibility with a wide range of tone delivery means, including the nasally inserted tube. The present invention is in particular ideally suited for use with the Talking Tracheostomy Tube, as described in U.S. Pat. No. 4,449,523 to Szachowicz et al, and with the Speaking Endotracheal Tube, as described in applicant's co-pending application Ser. No. 663,578, which application is incorporated herein by reference.

Another advantage of the present invention concerns the elimination of the drying problem that can be caused by pneumatic devices. In the present invention, the air flow is used primarily to amplify the tone and enhance the sound delivering ability of the particular delivery means. The airflow is not needed to vibrate the reed, the energy for that movement being provided by the pulse generator; thus, it was found that such amplifying and enhancing abilities could be achieved with an airflow substantially below that with which drying and air awallowing occur.

As previously stated, it has been found that various body fluids, such as saliva and mucous, can clog the delivery means, thereby preventing the tone from entering the oral cavity. In the present invention, the airflow is sufficient to retain this anit-clogging property.

Variation of the pitch of the tone is useful to match the tone to the particular acoustic qualities of the user's oral cavity, thereby maximizing the volume of the resultant speech. Pitch variation can also allow a speech frequency to be achieved that is similar to that of the individual's own voice, and can permit, in the hands of a skillful user, a method for creating an inflection in speech. Pitch variation is accomplished, in pneumatic devices, through decreases or increases in the air flow rate. In the present invention, pitch is varied by adjsting the frequency of the electrical signal produced by the pulse generator. This latter approach is more energy efficient, and keeps the airflow at a low level to ensure against drying problems.

The valve means of the present invention is designed to be in the closed position when not operating; thus, air does not flow unless a tone is being produced. As a result, the valve means of the present invention simultaneously produces the tone and controls air flow, thus elimating the need for a separate airflow control means.

The solenoid reed valve means in the present invention contains flexible and fixed reeds made of stainless steel. Operation of the valve involves producing a magnetic field so that the flexible reed is attracted to the fixed reed, thereby opening the valve. The magnetic field is created when the pulse generator sends an electrical signal through an electrical winding surrounding the outer housing of the valve. It was found that repeated operation of the valve with the current continually flowing in the same direction in the winding would cause the formation of a residual magnetic field in the reeds, causing less efficient valve operation or valve failure. To solve this problem, the pulse generator was modified to alternate the direction of current flow through the winding, thus eliminating the formation of any net magnetic field in the reeds.

The electrical pulse generating means has a witch means for actuating the valve means when the user desires to speak. However, many individuals who have need of an artificial speech aid do not have the physical ability to operate such a switch means in the noraml manner. Therefore, the pulse generating means includes a phone jack input to allow a means of connection with a remote switching means and thus, for bypassing the switch means. Such remote switch means include, for example, a forehead magnetic switch that would allow severly impaired individuals to actuate the valve means through movement of their brow.

It is therefore an object of the present invention to provide a novel pneumatic/electronic means of tone generation, such tone being suitable for use as a substitute vocal sound.

It is further an object of the present invention to eliminate the drying problems assiciated with pneumatic tone generation.

It is further an object of the present invention to vary the pitch of the tone without varying the rate of air flow.

It is further an object of the present invention to prevent clogging of the tone delivery means through use of a pressurized air flow.

It is further an object of the present invention to regulate airflow without the need for a separate device to do so.

It is further an object of the present invention to operate the solenoid reed valve means by alternating the direction of current flow so as to eliminate any undesirable magnetic effects and thereby extend the useful life of the solenoid valve means.

It is further an object of the present invention to allow for activation of the valve means by physically impaired individuals.

It is further an object of the present invention to be compatible with a wide range of tone delivery means, and be simple in design, thus easy and inexpensive to manufacture and use.

These and other further objects and advantages of the present invention will become clearer in light of the following detailed description.

DESCRIPTION OF THE DRAWINGS

The illustrative embodiments of the present invention may best be described by reference to the accompanying drawings where:

FIG. 1 shows the tone generator according to the teachings of the present invention, showing the electrical pulse generating means, and a cutaway view of the solenoid reed valve means.

FIG. 2 shows a schematic diagram of the electrical circuitry contained in the pulse generating means of the present invention.

FIG. 3 shows a schematic diagram of the battery means and the switch and input jack means of the present invention.

DETAILED DESCRIPTION OF THE PREFERRED EMBODIMENT

The electronic/pneumatic tone generator of the present invention is shown in FIG. 1 and consists essentially of a solenoid reed valve means, generally designated 10 and an electronic pulse generating means, generally designated 30.

To facilitate a complete understanding of the present invention, the basic elements of a solenoid reed valve are shown in the cutaway view of valve means 10 in FIG. 1. Valve means 10 includes housing 11 surrounded by winding 12. the essential internal elements of valve means 10, as seen in FIG. 1, include: flexible reed 13, fixed reed 14, reed supports 15 and 16, seal 17, and orifice 18. Fixed reed 14 and flexible reed 13 are secured to supports 16 and 15 respectively, and seal 17 is attached to flexible reed 13, as seen in FIG. 1. The basic operation of valve means 10 can now be appreciated. Valve means 10, as seen in FIG. 1, is in the closed position, as represented by the solid line of flexible reed 13 and seal 17, wherein seal 17 is in contact with and covering orifice 18. When an electrical current of sufficient strength passes through winding 12, a magnetic field is produced that attracts flexible reed 13, and seal 17, which is attached to flexible reed 13, to fixed reed 14, as represented by dashed line 19 in FIG. 1, thereby opening valve means 10. Stopping the current flow collapses the magnetic field, causing flexible reed 13 and seal 17 to return to the closed position. A substitute vocal tone is produced by actuating valve means 10 to a frequency of between 50 to 300 CPS; whereby the rapid movement of flexible reed 13 between the open and closed positions creates the sound. It can also be appreciated that when flexible reed 13 is in the open position, seal 17 is not contacting orifice 18, as represented by dashed line 19, as seen in FIG. 1. Thus, referring to FIG. 1, valve means 10 can regulate a flow of pressurized air, whereby pressurized air entering inlet end 20, from a pressurized air source (not shown) can pass through orifice 18 and exit valve outlet end 22 when valve means 10 is in the open position. It is this pressurized airflow that is used to amplify and carry the tone, thereby producing a resultant sound that is of sufficient strength to be compatible with a variety of tone delivery means. The tone delivery means, now shown, is connected to outlet end 22, seen in FIG. 1. Valve means 10 is a normally closed valve and will not permit airflow unless actuated to its open position.

Pulse generating means 30, as seen in FIG. 1, is connected to winding 12 by standard dual electrical cord 23 and produces the electrical signal needed to actuate valve means 10. Female plug 24 and male plug 25 provide for quick connection and disconnection of pulse generating means 30 to winding 12. Generating means 30 produces a pulsed signal that alternates between zero and +9 volts. In this manner, current flow is turned on and turned off actuating valve means 10 between the open and closed positions, as previously described. This pulsed signal is generated by pulsed current circuit means 35, which circuit is contained within generating means 30, and the schematic of which is seen in FIG. 2. Circuit 35, as seen in FIG. 2, contains "D" type flip-flop 36. The function of flip-flop 36 is to produce the pulsed signal needed to operate valve means 10. For purposes of explanation of the functioning of flip-flop 36, its Q output 37 will first be assumed to be high, at +9 volts, and its not-Q output 38 low, at ground potential. When Q output 37 of flip-flop 36 is high, current flows along line 39 and ultimately to valve means 10, as will be described in more detail at a later point in this description. Thus, valve means 10 remains in the open position, as shown by dashed line 19 in FIG. 1, as long as Q output 37 is high. The length of time Q output 37 is high is determined by the resistor-capacitor network or resistor 40 and capacitor 41, located on line 42, as seen in FIG. 2, the on-time of which, in the present case, is set at approximately 2 milliseconds. When current flowing from output Q 37 along line 42 charges capacitor 41 to approximately +4.5 volts, reset input R 43, connected to line 42, as seen in FIG. 2, is activated, forcing Q output 37 low and not-Q output 38 high. In addition, any residual voltage at reset input R 43 of flip-flop 36, and at resistor 40 and capacitor 41 is drained to Q output 37, which is now at ground, through forward biased diode 44 along line 45, seen in FIG. 2.

The length of time not-Q output 38 is high is determined by potentiometer 46 located on line 47, as seen in FIG. 2. By referring to FIG. 2, it can be seen that current from not-Q output 38, that flows while not-Q output 38 is high, will flow along line 47 through potentiometer 46, through resistor 48, charging capacitor 49. When capacitor 49 reaches approximately +4.5 volts, set input S 50 will be activated and not-Q output 38 will be forced low, and Q output 37 will be forced high. However, the time required to charge capacitor 49 to this threshold voltage is determined by potentiometer 46. Thus, the higher the resistance set at potentiometer 46, the longer it will take to charge capacitor 49 to the needed potential to trip set input S 50, returning Q output 37 high, and forcing not-Q output 38 low. It can now be appreciated that the frequency of the pulsed signal, sent along line 39 from output Q 37 and ultimately to valve means 10, is determined by the length of time not-Q output 38 is high, the duration of which is a function of the resistance setting of potentiometer 46. Frequency adjustment is needed so that the pitch of the tone produced by valve means 10 can be varied. Also, varying the amount of time current is not flowing to valve means 10 requires less energy than if frequency adjustment were accomplished by varying the amount of time current was flowing to valve means 10, i.e., the time that energy is being used to operate valve means 10. Any residual voltage at set input S 50 of flip-flop 36, and at potentiometer 46, resistor 48 and capacitor 49 is drained to not-Q output 38, which is again at ground, through forward biased diode 51 along line 52, seen in FIG. 2.

It can be appreciated by those skilled in the art that pulsed current circuit means 35 would be sufficient to operate valve means 10, either through use of a flip-flop circuit of sufficient electrical capacity to operate valve means 10 directly from its Q output or, for example, through the use of a switching transistor connected to one side of the valve winding, to deliver the needed current, with the opposite side of the winding at ground. However, it can be seen that such an arrangement would result in the current flowing through the valve winding in the same direction with each successive pulse. Such a delivery mode was found to leave a residual magnetic field in the metal reeds of valve means 10, causing less efficient valve operation or valve failure. Therefore, alternating current circuit means 55, as seen in FIG. 2, was included to alternate the direction of flow of each successive current pulse through the winding of valve means 10. Alternating the direction of current flow is accomplished in part by second "D"-type flip-flop 56, seen in FIG. 2. By referring to FIG. 2, it is seen that in flip-flop 56, clock input C 57 is connected to Q output 37 of flip-flop 36 by line 39; set input S 58 and reset input R 59 are tied to ground at point 66; and D input 60 is connected to not-Q output 61 by line 62. In this configuration, flip-flop 56 is an edge triggered device, wherein each positive edge entering clock input C 57 causes Q output 63 and not-Q output 61 to be alternately forced low and high. Thus, by referring to FIG. 2, the operation of flip-flop 56 can be explained if it is first assumed that if not-Q output 61 is high, at +]volts, then Q output 63 will be low, at ground potential, and current will flow along line 64. Upon the next positive edge entering clock input C 57, not-Q output 61 will be forced low, to ground potential, and Q output 63 will be forced high, and current will flow along line 65. Thus, each positive edge entering clock input C 57 alternates current flow between line 64 and line 65. Line 64 is connected to inputs 73 and 74 of AND gates 77 and 78 respectively, and line 65 is connected to inputs 71 and 72 of AND gates 75 and 76 respectively, as seen in FIG. 2. Also, inputs 67, 68, 69, and 70, of AND gates 75, 77, 78, and 76 respectively, are connected to line 79, as seen in FIG. 2. As line 79 is connected to line 39, as seen in FIG. 2, line 79 will be positive, with every positive edge entering input C 57, as will inputs 67, 68, 69, and 70. Therefore, inputs 71, 72, 73, and 74 actually determine the output state of AND gates 76, 76, 77, and 78, respectively, as it is these outputs that vary from positive to negative through connection to lines 64 and 65. It can now be appreciated how the direction of current flow through the winding of the solenoid reed valve used in the present invention can be alternated. Referring to FIG. 2, if Q output 63 is first assumed to be high, then not-Q output 61 is low, and thus, inputs 73 and 74 of AND gates 77 and 78, respectively, are negative, and inputs 71 and 72 of AND gates 75 and 76, respectively, are positive. Therefore, as transistors 80 and 81 are connected to AND gates 75 and 76, respectively, as seen in FIG. 2, transistors 80 and 81 are switched on. Thus, current will flow from point 82, at +9 volts, into collector 83 and out of emitter 84 of transistor 80, through the winding of valve means 10, represented schematically at point 90, in a direction from point 85 to point 86, and then into collector 87 and out of emitter 88 of transistor 81 to ground, at point 89.

At the next positive edge entering clock input C 57, Q output 63 goes from high to low, and not-Q output 61 goes from low to high. Thus, inputs 71 and 72 of AND gates 75 and 76 go from positive to negative, thereby turning off transistors 80 and 81, and inputs 73 and 74 go from negative to positive, thereby turning on transistors 91 and 92. Current can now flow from point 82 into collector 93 and out of emitter 94 of transistor 91, through the winding of the valve means 10, represented schematically at point 90, in a direction from point 86 to point 85, and then into collector 95 and out emitter 96 of transistor 92 to ground at point 89. Therefore, the direction of current flow through the winding of the solenoid valve is alternated with each successive positive edge entering clock input C 57 of flip-flop 56.

Each time current stops flowing through the winding of valve means 10, i.e. between each pulse, an inductive kickback occurs that could damage transistors 80, 81, 91, and 92. Therefore, forward biased diodes 97, 98, 99, and 100, as seen in FIG. 2, are used to suppress this kick-back.

Power is supplied to pulsed current means 35 and alternating current circuit means 55, by battery 101, from point 102, at +9 volts, as seen in FIG. 3, to points 103, 104, and 82, as seen in FIG. 2. The battery used in the present invention is a standard 9-volt "D" cell. ON/OFF regulation of power to circuits 35 and 55 is accomplished with switch means 105, seen in FIG. 3. In the present invention, switch means 105 is physically embodied as pressure-sensitive switch 32, located on housing 31 of electrical pulse generating means 30, as seen in FIG. 1. Also, pitch adjustment knob 33, as seen in FIG. 1, is used to operate potentiometer 46, seen in FIG. 2, thereby permitting manual adjustment of the pitch of the tone produced by valve means 10.

The full operation of the present invention can now be appreciated. Activation of pressure sensitive switch 32 supplies power to circuits 35 and 55, thus actuating valve means 10 to produce a tone. Simultaneously, pressurized air is allowed to flow through valve means 10 from a pressurized air source, not shown, attached to inlet end 20 of valve means 10, amplifying the tone produced therein. The tone and the pressurized air then enter the tone delivery means, not shown, connected to outlet end 22 of valve means 10, whereby the tone is delivered to the user's oral cavity, and is therein articulated into speech. The pressurized air or oxygen can be supplied by a hospital wall source or a compressed air or oxygen cylinder, with the airflow rate, in either case, being between 1 and 2 liters per minute.

To facilitate use of the present invention by physically impaired individuals, for whom activation of pressure sensitive switch 32 may present difficulty, input jack 106, as seen in FIG. 3, provides a means for bypassing the function of pressure sensitive switch 32, seen schematically at point 105 in FIG. 3, with a remote switch means, not shown. A remote switch means, such as a forehead actuated magnetic switch, can be plugged into input jack 106, at input jack access point 34, located on housing 31 of electrical pulse generating means 30, as seen in FIG. 1.

The suggested values of the resistances and capacities of the present invention are as follows: resistor 48–130K; resistor 40–300K. Capacitors 41 and 49 are 0.01 uf.

Various other electrical components of the present invention are more particularly described as follows: Diodes 44 and 51 are IN 4148 diodes. Diodes 97, 98, 99, and 100 are a capacitor bridge type VE 18X. Potentiometer 46 is rated at 1 Meg. ohm. Flip-flops 36 and 56 consist of a 4013 Dual-D CMOS IC. AND gates 75, 76, 77, and 78 consist of a 4081 QUAD-AND CMOS IC. Transistors 80, 81, 91, and 92 consist of a TPQ2222 QUAD Transistor.

Certain specific structures embodying the present invention have been described herein. However, it will be apparent to persons skilled in the art that possible various modifications or rearrangements of the parts as described may be made without departing from the spirit and scope of the underlying inventive concept of the invention described herein. Furthermore, the present invention is not limited to the particular forms shown and described, except as indicated by the scope of the appended claims.

What is claimed is:

1. An improved tone generator, for producing an artificial vocal tone, the tone suitable for delivery to a user's oral cavity by a tone delivery means enabling the user to articulate the tone into speech, which tone generator comprises:
  (a) solenoid reed valve means, for producing the tone and for regulating a flow of pressurized air through the valve means, the valve means having an inlet end connecting with a pressurized air source, and an outlet end connecting with the tone delivery means; and
  (b) electrical pulse generating means, electrically connected to the valve means, the generating means containing pulsed current circuit means, for producing a pulsed electrical signal for actuating the valve means at a sufficient frequency so that the valve means produces the tone, and so that the actuating of the valve permits the pressurized air to flow from the pressurized air source through the valve means amplifying the tone produced therein, the tone and pressurized air then entering the tone delivery means for delivery of the tone to the user's oral cavity wherein the tone is articulated into speech by the user.

2. The improved tone generator as defined in claim 1, wherein the electrical pulse generating means further includes, battery means for providing the electrical power needed to actuate the valve means, and electrical switch means, connecting the battery means to the pulsed current circuit means, for operating the valve means.

3. The improved tone generator as defined in claim 2, wherein the electrical pulse generating means further includes, frequency varying means, connected to the pulsed current circuit means, for varying the frequency of the pulsed electrical signal delivered to the valve means so that the pitch of the tone produced by the valve means can be regulated.

4. The improved tone generator as defined in claim 3, wherein the electrical pulse generating means further includes, input jack means, connected to the switch means, so that a remote switching means can be connected to the pulse generating means, bypassing the function of the switch means for providing remote operation of the valve means.

5. The tone generator as defined in claim 4, which electrical pulse generating means further includes alternating current means, connected to the pulsed current circuit means, for alternating the direction of the pulsed electrical current flow through the valve means for eliminating the formation of a residual magnetic field in the valve means.

* * * * *

UNITED STATES PATENT AND TRADEMARK OFFICE
CERTIFICATE OF CORRECTION

PATENT NO. :   4,612,664

DATED      :   September 16, 1986

INVENTOR(S) :  John J. Walsh, et al.

It is certified that error appears in the above-identified patent and that said Letters Patent is hereby corrected as shown below:

Col. 1, line 58, delete "overprolonged" and insert --prolonged--.

Col. 3, line 20, delete "awallowing" and insert --swallowing--.

Col. 3, line 25, delete "anit-clogging" and insert --anti-clogging--.

Col. 3, line 32, delete "infleciton" and insert --inflection--.

Col. 3, line 35, delete "adjsting" and insert --adjusting--.

Col. 3, line 45, delete "elimating" and insert --eliminating--.

Col. 3, line 62, delete "witch" and insert --switch--.

Col. 3, line 66, delete "noraml" and insert --normal--.

Col. 4, line 4, delete "severly" and insert --severely--.

Col. 4, line 11, delete "assiciated" and insert --associated--.

Col. 4, line 64, delete "the" and insert --The--.

Col. 6, line 64, delete "J" and insert --9--.

Col. 7, line 13, delete the first occurrence of "76" and insert --75--.

Col. 7, line 52, delete "kick-back" and insert --kickback--.

UNITED STATES PATENT AND TRADEMARK OFFICE
CERTIFICATE OF CORRECTION

PATENT NO. : 4,612,664

DATED : September 16, 1986

INVENTOR(S) : John J. Walsh, et al.

It is certified that error appears in the above-identified patent and that said Letters Patent is hereby corrected as shown below:

Col. 10, line 12, after the first occurrence of "current", insert the word --circuit--.

Signed and Sealed this
Thirtieth Day of December, 1986

*Attest:*

DONALD J. QUIGG

*Attesting Officer*  *Commissioner of Patents and Trademarks*